United States Patent [19]

Nogueira et al.

[11] Patent Number: 5,047,522
[45] Date of Patent: Sep. 10, 1991

[54] ISOLATED REPETITIVE DNA OF PROTOZOAN PARASITES

[75] Inventors: Nadia Nogueira, Princeton, N.J.; Paul Lizardi, New York, N.Y.

[73] Assignee: Rockefeller University, New York, N.Y.

[21] Appl. No.: 217,381

[22] Filed: Jul. 11, 1988

Related U.S. Application Data

[60] Division of Ser. No. 38,959, Apr. 16, 1987, Pat. No. 4,801,530, which is a continuation of Ser. No. 584,646, Feb. 29, 1984, abandoned, which is a continuation-in-part of Ser. No. 522,811, Aug. 12, 1983, abandoned.

[51] Int. Cl.$^5$ .................... C07H 15/12; C07H 17/00
[52] U.S. Cl. .......................... 536/27; 436/94; 436/6
[58] Field of Search .................. 536/27; 435/6

[56] References Cited

PUBLICATIONS

Wirth et al., Proc Natl Acad Sci 79: 6999–03 (1982).
Chen et al, Proc Natl Acad Sci 77(5): 2445–49 (1980).
Barrois et al, Proc Natl Acad Sci 78(6): 3323–27 (1981).

Primary Examiner—Robert A. Wax
Assistant Examiner—Scott Chambers
Attorney, Agent, or Firm—Felfe & Lynch

[57] ABSTRACT

Repetitive DNA sequences of the protozoan parasites *T. cruzi* and *P. falciparum* have been isolated. These sequences appear more than once in the parasitic organism. Once isolated, the DNA sequences may be labelled with materials such as chromogens, biotin, or radioactive substances. The sequences may be used, in labelled or unlabelled form, as probes for the parasites.

6 Claims, 5 Drawing Sheets

Specificity of hybridization of T. cruzi repetitive element.

Specificity of hybridization of T. cruzi repetitive element.

FIG. 4.

rPFR-1

TGTCCTCCAGACTTTTCTACCACTCGTAGAGTTTTCŤGGGTACTGTGAACTGACCTCCAGACTGATCTCT
ACAATCCGTAGAGTTCTǦGGTACTGTGAACTGTCCTCCCAGACTTTTCTACCACTCGTAGAGTTTCTGGG
TACTGTGAACTGACCTCCAGACTGATCTCTACAATCCGTAGAGTTACTǦGGTACTGTGAACTGACCTCC

2% pPFR-5

TTTTAGGTTTAGGGTTCAGGGTTTAGGGTTTAGGGTTCAGGGTTTAGGTTTÅGGTTCAGGGTTCAGGGT
TCAGGGTTTAGGTTTÅGGGTTCAGGGTTCAGGGTTTAGGTTTÅGGGTTCAGGGTTTAGGGTTTTCC

9%

ISOLATED REPETITIVE DNA OF PROTOZOAN PARASITES

This application is a divisional of application Ser. No. 038,959, filed Apr. 16, 1987, now U.S. Pat. No. 4,801,530 issued Jan. 31, 1989, which is itself a continuation of Ser. No. 584,646, filed Feb. 29, 1984, now abandoned, which is itself a continuation-in-part of Ser. No. 522,811, filed Aug. 12, 1983, now abandoned.

This invention concerns nucleic acid hybridization assays of biological samples for protozoan parasites utilizing hybridization probes constructed from species-specific repetitive nuclear DNA. The high sensitivity of these assays make them suitable for analysis of blood and other tissue specimen.

BACKGROUND

Protozoans which invade the blood stream and tissues of higher animals and live parasitically therein may cause serious diseases in the host. In fact, many of the diseases that have plagued mankind for centuries are due to protozoan parasites. African sleeping sickness, for example, is generally caused by *Trypanosoma brucei gambiense* which is spread by the bite of the tsetse fly, a blood-sucking insect. Another species of this genus, *Trypanosoma brucei brucei* infects domestic animals; death follows infection for horses, cattle and pigs. Kala-azar is a serious disease caused by *Leishmania donovani* which is spread by sand-flies. Chagas disease is widespread in tropical areas where *T. cruzi* infections occur.

A sensitive, rapid assay is needed for diagnosis of these diseases. Current techniques involve the isolation and cultivation of individual parasites which is time-consuming and often un-reliable (Chance, M. L., et al. Ann. Trop. Med. Parasitol. 68: 307 (1974); Martin, E., et al., Protozoology 23: 600 (1978); Miles, M. A., et al., Trans. R. Soc. Trop. Med. Hyg. 74, 243 (1979); Lainson, R., Trans. R. Soc. Trop. Med. Hyg., 75: 530 (1981)). Lesions due to infection by Leishmania species may be analyzed for parasites, by direct examination but this method does not allow identification of species causing more serious forms of the disease. Moreover other species, such as Tripanosomae do not express themselves in lesions and so require sensitive serological tests. The more reliable of those are difficult to use in large scale (immunofluorescence), or display cross-reactivity with other microorganisms (complement fixation, agglutination).

In addition, a major health problem has been created in areas of high infection when blood is collected for transfusion purposes. Since blood is a carrier of the parasites, blood from an infected individual may be unknowingly transferred to a healthy individual. Chagas disease, particularly, has been found to be a major problem for blood banks in countries where the disease is endemic, with many documented cases of transmission of the infection by blood transfusions. Current assays for these protozoan parasites have neither specificity nor sensitivity to detect parasites in blood and are thus not useful for screening of blood to be used for transfusion.

The economic toll to agriculture due to these protozoan parasites of domestic animals is immense. Infection by *Trypanosoma brucei*, for example, is fatal to cattle unless treated early in the course of disease. There is no currently available sensitive diagnostic assay for infection, so many animals are lost. Moreover, the effectiveness of chemotherapy in both humans and animals cannot be currently monitored so there is often needless reccurrence of the disease.

Wirth and Pratt (Proc. Nat'l. Acad. Sci. USA 79 6999 (1983) have described a hybridization assay for the detection of Leishmania parasites using probes to parasite kinetoplast DNA. This assay detects parasites in cutaneous lesions at a sensitivity level of 1,000–10,000 parasites per biopsy specimen. The specimens are collected by touch-blotting of nitrocellulose sheets over a small area of infected skin. However, this method is not sensitive enough to detect small numbers of parasites and relies on probes that have to be purified from the parasites themselves. This requires growth of these organisms in large quantities in the laboratory. Moreover, the method cannot be extended to parasites other than Trypanosomatidae, since these are the only ones to possess a kinetoplast.

A more sensitive assay has been sought for both Leishmania and other protozoan parasites which will be sensitive, specific, and thus be useful in early diagnosis of infection, will identify species of parasites more likely to induce severe disease, and aid evaluation of chemotherapy and screening of blood bank samples.

The complementary nature of the double-stranded DNA which comprises the genome plays a fundamental role in the duplication of the cell and in the transcription and translation of genetic information. In the laboratory, complementary strands of DNA may be readily dissociated, and under appropriate conditions of cation concentration, temperature, DNA concentration and fragment size, may be reproducibly re-associated. This complementary nature of DNA is the basis of a sensitive assay for genetic material. The Southern blot method, for instance, utilizes hybridization probes which are complementary DNA strands. A related assay, the Northern blot method, utilizes the ability of DNA to associate with complementary RNA probes. Detection devices employing RNA or DNA tagged with either a radioactive element or biotin have been developed (Gardner, L., Biotechniques March Volume 38 (1983); Langer, P. R., et al., Proc. Nat'l. Acad. Sci. U.S.A., 78 6633 (1981).

The reproducibility and reliability of the blot methods in general is due to the accuracy with which complementary strands recognize one another. However, each genome contains a large number of nucleotide pairs. The calf genome, for example, contains $3.2 \times 10^{19}$ nucleotide pairs (McCarthy, B. J., Progr. Nucleic Acid Res. Mol. Biol. 4, 129 (1965). It might seem that the probability of one chain finding and combining with its complement would be small. Surprisingly, however, it has been found that in genomes of some organisms the DNA occurs in repeated sequences that may account for a large proportion of the total genome (Britten, R. J. et al., Carnegie Inst. Wash. Year Book, 66, 73 (1967); ibid 65, 73 (1966)). Ten percent of the mouse genome, for example, consists of a million copies of a short nucleotide sequence (Waring, M. Et. al., Science, 154, 791 (1966)). It has been observed that many other species also contain repetitive DNA elements (Britten et al., Science 161, 529 (1968)).

Since the blot hybridization methods detect DNA sequences, it follows that sensitivity and specificity of assays are enhanced if a probe which recognizes a repetitive sequence can be obtained. Moreover, if this repetitive sequence is species specific, the probe recognizing it is also specific. Protozoan parasites containing such species-specific repetitive nuclear DNA elements have been sought.

SUMMARY

The present invention provides a method for detection of protozoan parasites in blood or other specimen from their mammalian hosts. The method comprises nucleic acid hybridization of repetitive nuclear DNA fragments of the parasites. Hybridization probes have been prepared for this purpose by cloning the repetitive nuclear elements that are species-specific in appropriate vectors. The sensitivity of these probes has been increased by further sub-cloning to make them capable of cascade hybridization. The assay is highly specific and sensitive for detection of disease-causing protozoan parasites of the commonly occurring Trypanosomatidae of the genus Leishmania and genus Trypanosoma, as well as for malaria-causing protozoae and other parasitic microorganisms of mammals.

DETAILS

We have discovered that protozoan parasites contain species-specific repetitive nuclear DNA elements.

The present invention provides a method for detection of protozoan parasites comprising nucleic acid hybridization with hybridization probes constructed from these species-specific repetitive nuclear DNA fragments.

The invention may be understood more fully in view of the accompanying Figures of which FIG. 1 illustrates the specificity of the *T. cruzi* repetitive element; and FIG. 2 illustrates the detection of parasites in the blood of humans infected with *T. cruzi*.

FIG. 4 illustrates the nucleotide sequence of the repetitive DNA from clones pPFR-1 and pPFR-5.

Availability of DNA Hybridization Probes

Figure 1:
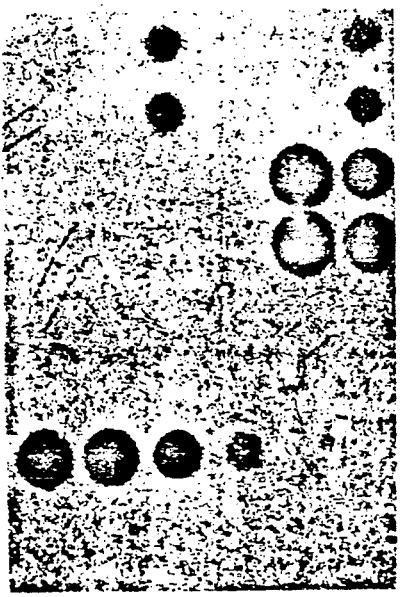

Clones comprising repetitive nuclear DNA fragments specific for protozoan parasites disclosed in the present invention are deposited with The Rockefeller University, 1230 York Avenue, New York, N.Y. 10021. Preferred clones of the present invention comprising repetitive nuclear DNA fragments specific for *T. cruzi* and for *P. falciparum* are also deposited at the American Type Culture Collection, Bethesda, Md. and bear the following deposit numbers:

| Clone # | ATCC # |
|---|---|
| pTC-NRE | 40078 |
| pTC multi-NRE | 40077 |
| pPFR-1 | 39619 |
| pPFR-5 | 39618 |

Deposit is for the purpose of enabling disclosure only and is not intended to limit the concept of the present invention to the particular materials deposited.

Isolation Identification and Synthesis of Species-Specific Repetitive Nuclear DNA Fragments Repetitive nuclear DNA fragments have been isolated from protozoan parasites by the following method:

a. Parasite DNA was sheared by sonication to an average size of 1,500–2,000 base pairs, and then denatured with alkali.

b. The DNA solution was neutralized, and the single strands were allowed to renature to a Cot of 2.0 (Balton et. al., Carnegie Inst. Wash. Year Book, 65, 78 (1965)).

c. The rapidly-renatured (Cot 2.0) DNA fraction was treated with S1 nuclease to destroy residual single-stranded DNA.

d. The repetitive DNA was made blunt-ended by treatment with Klenow DNA polymerase I, and was then joined to Bam HI linkers (Deininger, P. et al., J. Mol. Biol. 151, 17 (1981)). This DNA was then ligated to a suitable vector (PUC 13 or pBR 322) and used to construct a library of repetitive DNA elements. The library was stored in multiple replicas (nitrocellulose filters containing 1000 colonies/filter).

e. A DNA probe from the same parasite was prepared by nick-translation (2) of total parasite DNA. Other probes are prepared by nick-translation of total DNA from other parasites or from vertebrate hosts of interest. Whole DNA should be screened for cross-reactivity with the clones from the primary parasite.

f. Identical library replicas containing repetitive DNA clones (500–1,000 colonies/filter) were hybridized as follows:

With labeled total DNA from the same parasite Hybridization for a short period of time (1 hr.) is used to identify clones with the highest repetitivity.

With labeled DNA from other parasites, or from vertebrate hosts of interest. Hybridization is allowed to proceed to completion (24 hour) to achieve maximum sensitivity.

g. Clones were selected which give maximum hybridization signal with the primary parasite, and yet show no evidence of cross-reactivity.

h. The clone was modified, if necessary, by addition of extra repetitive DNA of the same kind or a combination of repetitive DNAs from other genes to insure that the resulting probe will be capable of cascade hybridization.

i. Combination probes may also be constructed to comprise a tandem linear assay of nuclear and/or kinetoplast repetitive elements.

j. The probe was tested in hybridization assays similar to those described for *T. cruzi* and *P. falciparum*.

The method outlined above have been applied to the parasites *Leischmania brasiliensis, L. Tropica, L. mexicana*, and *L. donovani. T. cruzi, T. brucei brucei, T. brucei gambiense* and *Plasmodium falciparum* and may be applied to other protozoan parasites as well.

Repetitive DNA fragments from other protozoan parasites of the same genus and from related genera may be isolated by the same and similar methods. Examples include, but are not limited to Trypanosomatidae parasites of the genus Leishmania and Trypanosoma, as well as organisms of the genus Plasmodi and Babesia. Leischmania parasites, for example, comprise *L. donovani, L. brasiliensis, L. tropica*, and *L. mexicana*. Trypanosomae may be Salivarian or Stercorarian. Salivarian trypanosomes comprise *T. brucei, T. congolense*, and *T. vivax*. Stercorarian trypanosomes comprise *T. cruzi*. Also included are filarial parasites comprising *Wuchereria Bancrofti* and *Brugia malayi*, and the human malaria-causing parasites *P. malaria, P. vivax*. DNA from the commonly occurring blood parasites of mammals and amoebae from feces may also be isolated by the given method or others known in the art and used as hybridization probes in the assays of the present invention.

The repetitive nuclear DNA element isolated from *T. cruzi* has been analyzed for nucleotide sequence and found to be as follows:

CTCTTGCCCACACGGGTGCTGCACTCGGCTGATCGTTTTCGAGCGGCT
GCTGCATCACACGTTGTCGTCCAAATTTTTGTTTCCGATTGTGAATGGTG
GCAATCGGAAACACTCTCTGTCAATATCTGTTTGCGTGTTCACACACTGGA
CACCAAACAACCCTGAACTATCCGCTGCTTGGAGGAATTTCGCGAG

This DNA element exhibits micro-variations. However, although this sequence varies 5-20% at individual positions, it still is a species-specific hybridization probe for *T. cruzi*. It is to be understood that the hybridization probes of the present invention comprise these variations.

Six independent clones of *P. falciparum* DNA have been isolated using the plasmid pUC13 as vector. The clones, which have been named pPFR-1 through pPFR-6, contain inserts with sizes ranging from 280 to 1200 base pairs (BP), approximately. The cloned inserts are displayed in FIG. 1 as stained DNA bands in an agarose gel. Table I shows the approximate sizes of each of the cloned inserts. The table also shows that clones 3, 4, and 5 belong to the same sequence family. Clones 1, 2 and 6 are, all different from each other and from the C. family. The abundancy of C-family clones suggests that they represent the major repetitive element of *P. falciparum*.

Figure 2:
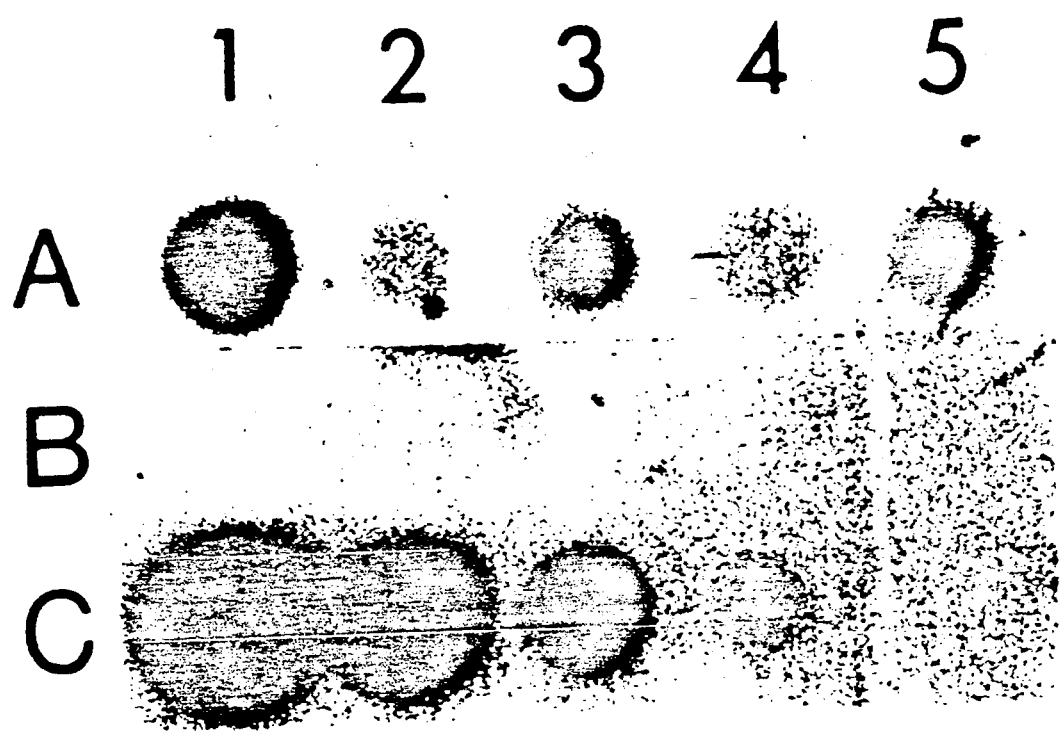
Figure 3:
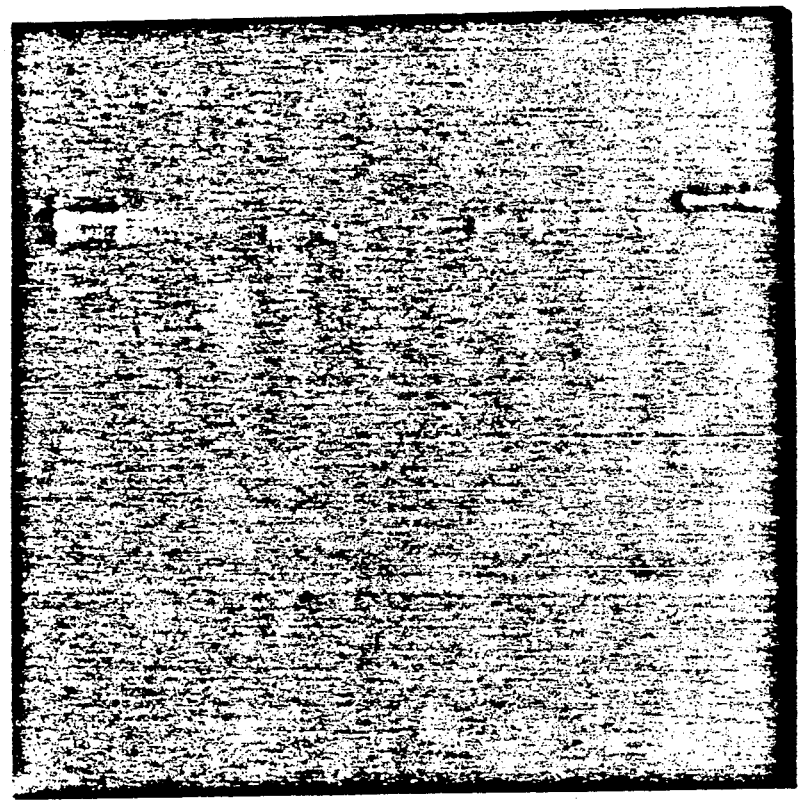
FIG. 3 illustrates the analysis of cloned *P. falciparum* DNA inserts by agarose gel electrophoresis.

The DNA of clones pPFR-1 and pPFR-5 has been sequenced. FIG. 2 shows that the basic repeating unit of pPFR-1 is a 51 bp sequence, while for pPFR-5 the repeating unit is 21 bp. The repeating units show small imperfections, or sequence microheterogeneities.

TABLE 1

| P. FALCIPARUM REPETITIVE DNA CLONES | | |
|---|---|---|
| | Insert size | Sequence Family* |
| pPFR-1 | 1200 | A |
| pPFR-2 | 800 | B |
| pPFR-3 | 280 | C |
| pPFR-4 | 320 | C |
| pPFR-5 | 340 | C |
| pPFR-6 | 950 | D |

*Sequence family relationships were determined by hybridization of labeled DNA from each clone with Southern blots containing DNA from all six inserts.

The DNA sequence may be synthesized by methods well known in the art either chemically or biologically. DNA complementary to this sequence and RNA having the same or complementary sequence may be similarly synthesized.

DNA sequences may also be constructed which consist of repeats of the repetitive element, or repeats of a sub-domain of the element. A third possibility is the construction of mixed element clones, containing tandem repeats of various elements (a, b, c ...) in the form a-a-a ... - b-b-b ... c-c-c .... Likewise, multi-a multi-b, and multi-c clones may be constructed independently, and mixed at the time of the tagging reaction.

When tagged with a radioactive element preferably $^{32}P$, or biotinylated, the natural or synthesized repetitive DNA and RNA are useful in a hybridization assay for the species from which they were first isolated. These repetitive DNA elements do not appear to be from structural genes nor do they appear to code for any known structural products such as proteins.

Preparation of hybridization probes

Hybridization probes for protozoan parasites may be prepared by cloning the nuclear repetitive elements that are species-specific in a suitable vector and labeling with a suitable label.

Vectors into which the DNA element may be inserted and replicated are suitable. Such vectors comprise, for example, *E. coli* plasmids, filamentous phages, lamboid bacteriophage, cosmids and yeast shuttle vectors. Other vectors known in the art may be employed. Especially preferred is the plasmid pUC 13.

For purposes of the DNA hybridization assay the clones are labeled with either a radioactive element or a chromogen, or biotin. The clones may be labelled, for example, with $^{32}P$ by nick-translation with DNA polymerase in the presence of $^{32}P$-dcTP (Botchan, M., et. al. Supra)

Alternatively, in assays utilizing RNA hybridization, tagged RNA complementary to the repetitive DNA is prepared.

Appropriate promoter sequences may be fused to the DNA of interest and replicated in an appropriate host such as *E. coli* using standard cloning techniques. This DNA may then be isolated from the *E. coli* and incubated in vitro with RNA polymerase to generate radioactive or biotinylated RNA. The method of Green, M. et al. (Cell 32, 681 (1983)), for example, may be used to generate biotinylated or radioactive RNA complementary to the repetitive nuclear DNA.

The hybridization probes containing species-specific nuclear repetitive DNA may be further modified by addition of extra repetitive DNA to ensure that the resulting probe is capable of cascade hybridization in DNA/DNA hybridization assays. Because of the formation of multiple-concatenamer DNA networks due to the cascade hybridization signal, the sensitivity of the assay is significantly increased. The hybridization probes with cascade signal may detect DNA equivalent to as little as one parasite because the hybridization signal is amplified. This increased sensitivity makes the assay suitable for early diagnosis of infection or for blood bank screening and useful in the monitoring of chemotherapy directed at eliminating known infections.

Nucleic Acid Hybridization Assay

The assay for protozoan parasites may be performed on any biological sample suspected of containing the parasite. Blood, for example, or biopsy tissue or matter from lesions obtained by blot or wash are suitable samples for assay. Because of its sensitivity, the method of the present invention may be applied to blood where as little as one parasite per specimen may be detected.

In the method of the present invention, the parasite DNA isolated from a tissue biopsy specimen or body fluid by phenol extraction (Lizardi, P. et al., Methods in Enzymology, Vol. 96 "Biomembranes" Eds. S. Fleisher and B. Fleisher; Academic Press, N.Y.) or a small tissue biopsy, body fluid or parasite culture sample which can be efficiently solubilized in alkali (without prior phenol extraction) is spotted on nitrocellulose or similar solid support such as gene-screen using dot-blot methodology (Kafatos et al., Nucleic Acids Research, 7, 1541 (1979)). After DNA binding, the nitrocellulose or other solid support is contacted with radioactive probe under conditions suitable for reaction between probe and bound DNA. The nitrocellulose, for example, may be incubated in the presence of hybridization solution (Kafatos, et al., Supra) at an appropriate temperature, about 46° for about 4 to 20 hours. The nitrocellulose is removed from solution, washed and, when a radioactive probe has been applied, is exposed radioautographically using X-ray film and intensifying screens. A signal is observed as dark spots on the film after 4–24 hour exposure. When the probe is biotinylylated the nitrocellulose is exposed to an avidin-enzyme system and observed for colored spots indicative of parasite DNA.

The specificity of the assay may be tested by contacting other protozoan parasites with the probe. Control samples of known parasite DNA may be run concurrently for comparison.

The invention may be illustrated by the following examples, but is not intended to be limited thereby.

EXAMPLE 1

This example illustrates the isolation and identification of the repetitive nuclear DNA element from *T. cruzi*. *T. cruzi* epimastigote DNA was cut with a variety of restriction enzymes. Digestion with SST I generated a coherent band of about 200 base pairs which contained seven to ten percent of the total parasite DNA. The element contains a 195 base pair domain bounded by SST I sites, but the actual length of the repetitive sequence may be somewhat longer. Southern blot analysis using the radioactive repetitive probe showed that at least some of the repetitive elements occur in tandem domains. Since this repetitive element is repeated about 100,000 times in the *T. cruzi* genome, it provides the basis for a hybridization assay capable of detecting a fraction of a picogram of parasite DNA.

The sequence was used to derive the expected thermal stability (Tm) of the DNA. The Tm of 90.4° C. identified this DNA as being of nuclear origin, since kinetoplast DNA is known to have a much lower Tm.

EXAMPLE 2

This example illustrates the preparation and specificity of hybridization probes capable of generating a cascade hybridization signal in a DNA/DNA hybridization assay.

The repetitive nuclear DNA element from *T. cruzi* (Example 1) was isolated after separation from the digestion medium by a 1.5% agarose gel and cloned in the plasmid pUC 13 (Vieira, J., et al., Gene 19, (1983)). The clone was named pTCNRE (plasmid *T. cruzi* - nuclear repetitive, element). Other clones were constructed which contained not one, but several copies of the element. These new clones were termed pTC-multi NRE and are capable of generating a hybridization signal which will be amplified about 40 fold by cascade hybridization.

Hybridization probes were constructed by labeling pTCNRE by nick-translation with DNA polymerase in the presence of $^{32}$P-dcTP (Botchan, M., et al. supra) yielding a specific activity of $10^8$ CPM per microgram.

The *T. cruzi* probe hybridized with all of the eight *T. cruzi* strains tested. Hybridization was negative with mouse or human DNA.

FIG. 1 illustrates the specificity of the *T. cruzi* hybridization probe. The probe detected *T. cruzi* in epimastigotes and the blood stream forms, but was negative for *L. donovani, L. tropica, L. braziliensis, L. mexicana, T. evansi, T. equiperdum, T. brucei brucei, T. lewisi* and *T. congolense*.

EXAMPLE 3

This example illustrates the assay of blood for *T. cruzi*.

*T. cruzi* DNA (isolated from epimastigotes by phenol extraction) was spotted on nitrocellulose using dot-blot methodology (Kafatos, et al., Supra). This technique, which is well described in the cited reference simply involves denaturation of DNA in alkali, neutralization, and spotting on nitrocellulose in the presence of high salt (NaCl) concentrations. Amounts of *T. cruzi* DNA ranging from 0.01 ng (equivalent to 30 organisms) to 10 ng (30,000 organisms) were spotted to provide a series of standards. Two kinds of experimental samples can also be spotted on nitrocellulose: (a) Any kind of DNA obtained from a tissue biopsy or body fluid by phenol extraction. (b) Any small tissue biopsy, body fluid, or parasite culture sample (1 ul to 5 ul) which can be efficiently solubilized in alkali (without prior phenol extraction). Samples to be bound are conveniently organized using a 8×12 well Hybry-dot apparatus (Schleicher and Schuell, Inc., Keene, N.H.) which aligns spots of about 5 mm diameter on the nitrocellulose. After DNA binding, the nitrocellulose was baked for 2 hours and then placed in a plastic bag containing hybridization solution (3). Radioactive probe pTC NRE (from Example 3) was added, the bag was sealed, and incubated at the appropriate temperature (46° C.) for 4–20 hours. The nitrocellulose was then taken out of the base and washed several times in low salt-sodium dodecyl sulfate solution. Finally, it was exposed radioautographically using X-ray film and intensifying screens. A signal was observed as dark spots in the film after 4–24 hour exposure.

The assay with pTC-NRE plasmid detected DNA equivalent to about 30 parasites. The pTC multi-NRE plasmids detect DNA equivalent to 1 parasite because the hybridization signal is amplified about 40-fold by cascade hybridization (formation of multi-concatenamer DNA networks).

The pTCNRE assay is species-specific. Tests with different *T. cruzi* strains have been positive with all strains tested. The sensitivity of the assay was found to be sufficient to detect one *T. cruzi* cell in a background of 0.3 cc blood. The results of assay of blood of five individuals throught to be infected with *T. cruzi* are illustrated in FIG. 2. All five individuals showed positive hybridization whereas normal human blood gave negative results.

EXAMPLES 4–7

The method of Example 3 may be used to assay blood for *Leishmania brasiliensis, L. tropica, L. mexicana* or *L donovani*. Blood, tissue biopsy or body fluids may be assayed by the method of Example 3 for any protozoan parasites.

EXAMPLE 8

This Example illustrates a method of generating biotinylylated or radioactive RNA complementary to the species-specific repetitive nuclear DNA.

A piece of DNA containing Salmonella phage Sp6 promoter sequences is fused to the DNA clone of interest. This new DNA construction can be replicated in *E.*

*coli* using standard cloning techniques. This DNA is then isolated from *E. coli*, and incubated in vitro with RNA polymerase (obtained from Salmonella phage SP6) and used to generate radioactive or biotinylylated RNA.

EXAMPLE 9

This example illustrates the method by which the species specificity of repetitive nuclear DNA elements from a particular protozoan parasite was established.

1. Total DNA was isolated from a protozoan parasite of interest and labeled by nick-translation. DNA from other parasites or from a vertebrate host was likewise isolated and labeled.

2. Repetitive DNA elements from the protozoan parasite was cloned in suitable vectors and affixed to nitrocellulose to form library replicas upon which DNA were identically located. A first replica was hybridized with radio-active labeled DNA from the same parasite. A second replica was hybridized with labeled DNA from other parasites or from the vertebrate host.

3. The hybridized replicas were exposed to film for a time sufficient to produce development of radioactive areas corresponding to hybridization with labeled DNA.

4. The exposed films were superimposed and aligned in accordance with the location of clones in the replicas.

5. Many areas showed development in both replicas which indicated cross-reactivity between the species. However, some areas showed development in only the one replica containing the parasite of interest. This indicated species-specific DNA.

6. Those species-specific clones which gave maximum hybridization signal with the parasite of interest but not with other parasites or the host were selected and used as hybridization probes for this parasite.

EXAMPLE 10

This example illustrates the use of DNA hybridization probes to detect *P. falciparum* in blood.

Figure 5:
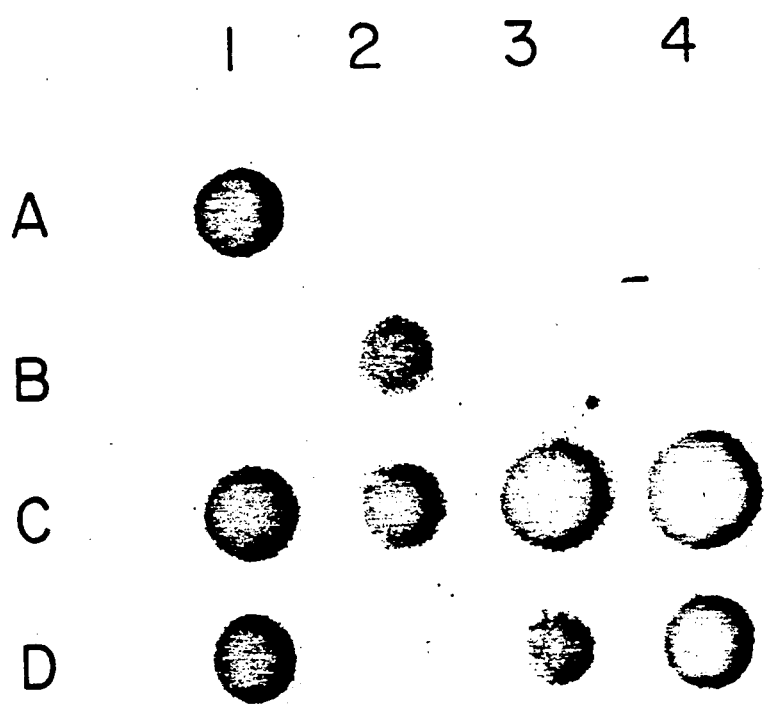
FIG. 5 illustrates the detection of *P. falciparum* DNA from blood samples using dot blot hybridization.

Clones pPFR-1 and pPFR-5 have been used in a hybridization assay to detect the presence of *P. falciparum* in blood. A mixture of the two DNA's was labeled by nick-translation and hybridized with a nitrocellulose sheet containing phenol-extracted DNA from infected as well as uninfected human blood. Known amounts of *P. falciparum* DNA were used as controls for quantitation. FIG. 5 illustrates the results of these experiments.

The DNA standards show that the sensitivity of this assay corresponds to about 1 ng of *P. falciparum* DNA. With appropriate optimization the assay can detect 0.1 ng of DNA, which corresponds to the DNA content of $3.3 \times 10^3$ parasites. This sensitivity is adequate to detect parasites in the blood of an infected patient, provided that the assay is carried out after the parasites have come out of the liver and entered erythrocytes. Typical blood parasitemia levels in human range from $4 \times 10^3$ parasites/ml at very early stages up to $4 \times 10^8$ parasites/ml in the acute stages. A level of 5,000 parasites per ml. would be easily detected by the hybridization assay, but would be virtually impossible to detect by conventional microscopic examination of blood (this level roughly corresponds to one infected erythrocyte for every $10^6$ erythrocytes).

Compared to a light microscopic parasitemia count, this assay provides about 500-fold more sensitivity, and does not require an expert observer. The method is particularly suitable for the testing of anti- *P. falciparum* chemotherapies. It is also ideally suited for the measurement of parasitemia in post-vaccination challenge experiments.

EXAMPLE 11, 12

*T. brucei gambiense*

We have hybridized nitrocellulose filters containing copies of clone libraries from each of these two parasites. Using the methods described in Example 9, we have isolated species-specific repetitive element clones. These clones have been frozen for further testing.

The clones in our possession include one clone containing DNA identical to that described by Sloof et al. (Sloof, et al., Nucleic Acids Res. 11, 3889 (1983)) hereinafter termed Sloof DNA incorporated by reference.

EXAMPLES 13, 14

We have existing frozen clone libraries containing repetitive elements (Kinetoplastic as well as not kinetoplastic) of *Leishmania tropica* and *Leishmania brasiliensis*.

EXAMPLE 15

The methods of the present invention may be extended to other important parasites. The repetitive nuclear DNA elements may be isolated, identified as species-specific and used as hybridization probes as disclosed hereinabove. Examples include:

*T. equiperdum*
*T. vivax T. rhodesiense T. congolense Babesia boris Wuchereria bancroft Brugia malayi*
*Entamoeba hystolitica Plasmodium malariae*
*Theileric parva*

What is claimed:

1. Isolated *T. cruzi* DNA which is repeated more than once in the organism and
   (a) has nucleotide sequence 5'-CTCTTGCCCACACGGGTGCTGCACTCGGCTGA
   TCGTTTTCGAGCGGCTGCTGCATCACACGTTG
   TCGTCCAAATTTTTGTTTCCGATTGTGAATGGTG
   GCAATCGGAAACACTCTCTGTCAATATCTGTT
   TGCGTGTTCACACACTGGACACCAAACAACCCTGA
   ACTATCCGCTGCTTGGAGGAATTTTCGCGAG-3' or (b) the nucleotide sequence complementary to it or its double stranded form.

2. Isolated *P. falciparum* DNA which is repeated more than once in the organism and
   (a) has nucleotide sequence 5'-TGTCCTCCAGACTTTTCTACCACTCGTAGAGTTTCTGGGTACTGTGAACT
   GACCTCCAGACTGATCTCTACAATCCGTAGAGTTTCTGGGTACTGTGAACT
   GTCCTCCAGACTTTTCTACCACTCGTAGAGTTTCTGGGTACTGTGAACTGA
   CCTCCAGACTGATCTCTACAATCCGTAGAGTTACTGGGTACTGTGAACTGA
   CCTCC-3' or

-continued

5'-TTTTAGGTTTAGGGTTCAGGGTTTAGGGTTTAGGGTTCAGGGTTTAGGTTTAGGGTTCAGGGTTCAGGGTTCAGGGTTTAGGTTTAGGGTTCAGGGTTAGGTTTAGGGTTCAGGGTTTAGGGTTTTCC-3' or (b) the nucleotide acid sequence complementary to it or its double stranded form.

3. The isolated *T. cruzi* DNA of claim 1, further comprising a label.

4. The isolated *P. falciparum* DNA of claim 2, further comprising a label.

5. The isolated *T. cruzi* DNA of claim 3, wherein the label is radioactive, is a chromogen, or is biotin.

6. The isolated *P. falciparum* DNA of claim 4, wherein the label is radioactive, is a chromogen, or is biotin.

* * * * *